Figure 1:
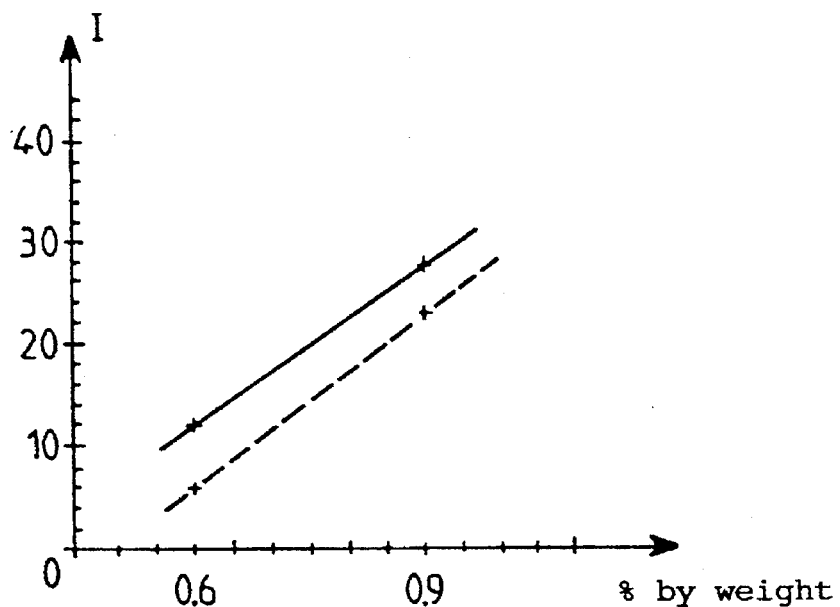

United States Patent [19]

Nadaud

[11] Patent Number: 5,635,171
[45] Date of Patent: Jun. 3, 1997

[54] COSMETIC OR PHARMACEUTICAL COMPOSITION IN THE FORM OF A RIGID GEL, PARTICULARLY FOR CONTAINING INCLUSIONS THEREIN

[75] Inventor: Jean-Francois Nadaud, Paris, France

[73] Assignee: L'Oreal, Paris, France

[21] Appl. No.: 418,612

[22] Filed: Apr. 7, 1995

Related U.S. Application Data

[63] Continuation of Ser. No. 78,304, Oct. 7, 1993, abandoned.

[30] Foreign Application Priority Data

Dec. 21, 1990 [FR] France ................... 90 16099

[51] Int. Cl.$^6$ ..................... A61K 31/78; A61K 7/00
[52] U.S. Cl. ................. 424/78.03; 424/78.02; 514/944; 514/938
[58] Field of Search ............... 424/401, 78.03, 424/78.02; 514/944, 938

[56] References Cited

U.S. PATENT DOCUMENTS 4,761,288  8/1988  Mezia .
4,897,269  1/1990  Mezia .
4,992,476  2/1991  Geria .

FOREIGN PATENT DOCUMENTS 0177223   4/1986   European Pat. Off. .
0336900  10/1989   European Pat. Off. .
0346097  12/1989   European Pat. Off. .

*Primary Examiner*—Sallie M. Gardner
*Attorney, Agent, or Firm*—Cushman Darby & Cushman Intellectual Property Group of Pillsbury Madison & Sutro LLP

[57] ABSTRACT

A transparent or translucid gel based on a cross-linked polyacrylic acid type polymer is rigidified by at least one galactomannan (carob, guar or tara gum) in small quantity. The gel then has a sufficiently rigid consistency to ensure good stability therein of inclusions consisting of a water-in-oil or oil-in-water emulsion, a gel or an aqueous dispersion of lipid vesicles. The presence, in the medium, of salts, which are otherwise incompatible with the polymer, does not disrupt the rheological state of the gel.

13 Claims, 2 Drawing Sheets

COSMETIC OR PHARMACEUTICAL COMPOSITION IN THE FORM OF A RIGID GEL, PARTICULARLY FOR CONTAINING INCLUSIONS THEREIN

This is a continuation of application Ser. No. 08/078,304, filed Oct. 7, 1993, now abandoned.

The present invention relates to a cosmetic or pharmaceutical composition which is provided in the form of a gel which remains rigid during storage even when it is contained in jars or the like of large volume but which is capable of becoming free-flowing again during application thereby giving a product of cosmetic quality, that is to say which is mild and non-sticky.

There recently appeared on the market cosmetic compositions containing two viscous phases (A) and (B), the so-called internal phase (A) being arranged in the form of at least one inclusion inside the so-called external phase (B). The phase (A) may be provided in the form of a thickened or gelled aqueous formulation, of an oil-in-water or water-in-oil emulsion, of an aqueous dispersion of vesicles consisting of ionic or nonionic lipid layers encapsulating an aqueous phase, or alternatively liquid crystals. For example, colored products can be injected into transparent gels, producing a wide variety of designs inside the gel. In this case, it is important for the external phase to be perfectly rigid and stable in order to avoid any deformation of the design or the style of drawing which the inclusion(s) forms (or form) during transportation or handling of the product.

Moreover in general, it may, in certain applications, be necessary to formulate transparent, colorless, stable and rigid gels.

A composition consisting of a mixture of a polygalactomannan gum and a copolymer based on a dicarboxylic anhydride containing an alpha,beta-olefin unsaturation and a comonomer chosen from hydrocarbons containing an alpha-olefin unsaturation and alkyl vinyl ethers is known via U.S. Pat. No. 4,143,007. This composition is described as providing an exceptionally high viscosity to an aqueous solution because of a synergistic viscosity effect resulting from the interaction of the polygalactomannan and the components of the copolymer. A composition comprising a mixture of guar gum and a polyacrylamide, described as providing, when it is added to an aqueous medium, a synergistic increase in the viscosity of the medium, is also known via U.S. Pat. No. 3,658,734. However, in practice, the polymer mixtures of the two American patents mentioned above give opaque and turbid gels which remain free-flowing. Document FR-A 0,346,097 describes a liquid system containing a thickening mixture consisting of a mixture of a gum type polymer and an acrylic type polymer. This mixture has the advantage of giving a gel having a high viscosity; but it is not specified in this document that some of these mixtures make it possible to obtain gels which remain rigid even when they are contained in jars or the like of large volume, for example greater than 50 ml.

Thickening and/or gelling agents, which are the most appropriate for the preparation of transparent, colorless gels, are carboxyvinyl polymers which are well known and widely used especially in the cosmetic field. By way of example, there may be mentioned the cross-linked polyacrylic acids marketed under the names "CARBOPOL 934, 940 and 941" by the company GOODRICH. If a carboxylic polymer alone is introduced, it is necessary, in order to obtain a yield point and a consistency which make it possible to prepare a rigid product which can be stored, to add a quantity of carboxylic polymer such that the product obtained is no longer cosmetic during the application.

The applicant has sought a solution to this problem and it has discovered, surprisingly, that the combination of at least polygalactomannan, in a very small amount, with a gel obtained with a carboxyvinyl monomer-based polymer as gelling agent, makes it possible to increase the yield point and the consistency, that is to say the rigidity, sufficiently so that rigid gels can be obtained which preserve this characteristic even when they are contained in jars or the like of large volume, especially greater than 50 ml and which, during application, give through shearing a mild and non-sticky product; in other words, during application, the product is not too viscous, which could not be predicted from the results observed with the compositions of U.S. Pat. No. 4,143,007; U.S. Pat. No. 3,658,734 and EP-A 0,346,097. It is thus possible to prepare rigid, virtually solid gels optionally containing stable inclusions of liquid or viscous phases, such gels being contained in jars or the like of large volume ranging for example up to about 250 ml. These gels can then be applied to the skin without giving, through shearing a gel which is too viscous and which would be sticky and would not therefore be usable in cosmetics. According to the process of the invention, there is therefore an increase in the yield point without troublesome increase in the viscosity after shearing. It should be noted that this result cannot be obtained with polysaccharides other than polygalactomannans, such as xanthan gums. Moreover, the applicant has discovered equally surprisingly that this combination makes it possible to correct or limit the incompatibility, with certain salts, of gels based on such polymers, an incompatibility which manifests itself even if these polymers are neutralized.

Carob gum, guar gum and tara gum may be used as polygalactomannan. Carob gum is preferably used.

Carob gum is a well-known product used in food and cosmetic products. Solutions of carob gum up to 0.5% by weight are in liquid form. At 1% by weight, the liquid is slightly viscous or is gelatinous. Carob gum is known to be able to influence the gelling properties of carrageenan and agar gels for the purpose of making them more elastic and increasing their breaking stress. Moreover, it has been combined with other gums, for example with xanthan gum, in particular in order to form a binding agent which can be used in pharmacy (JP-A 79/070 420) in order to form a gelled medium for the treatment of burns (FR-B 2,085,737) or in order to form gellable and gelled compositions containing agar combined with a xanthan-carob combination (U.S. Pat. No. 3,700,451 and U.S. Pat. No. 3,944,427), and with guar gum, in particular in order to form cosmetic compositions for cleansing (JP-B 85/112 712, JP-B 85/197 798 and JP-B 85/197 799). Tara, guar and carob gums are known in their combinations with a calcium or aluminum alginate, in particular in order to form aqueous cosmetic lotions (U.S. Pat. No. 3,764,707).

Moreover, there may be mentioned that the introduction, into an anti-inflammatory ointment, of a gelling and/or thickening agent chosen from a group comprising, inter alia, carob gum and polymers based on carboxyvinyl monomers is envisaged in Japanese Patent Application JP-A 87/039 524. However, a combination of a carboxyvinyl polymer and carob gum never appears in the examples of this patent application.

Finally, a liquid product for cleansing is known via European Patent EP-B 67 025 in which a surface-active agent, guar gum and a carboxyvinyl monomer-based polymer are combined. Although the combination of a galactomannan with such a polymer is described in this patent, the presence of a surface-active agent modifies the nature of the problem to be resolved. Indeed, the instability of the guar gum-based cleansing compositions which is described in this patent, an instability which is avoided by virtue of the addition of the said polymer, is due to the presence of a surface-active agent. Moreover, they are liquid compositions and the special rheological properties of the combination are therefore never mentioned.

The applicant has now observed unexpectedly that by combining a polygalactomannan with carboxyvinyl polymers, unexpected modifications of the rheological properties of the latter occur which make it possible to resolve the problems described above, which problems resulted from the use of the said carboxyvinyl polymers used alone. The gels obtained are transparent and they possess completely satisfactory cosmetic characteristics during application. They have an astonishing rheological behavior: after standing for about 48 hours, they behave like a solid, in the rheological sense of the term, up to the yield stress, and the solid/liquid transition for these gels is much higher than for the average gel. Consequently, they can physically stabilize all the phases in suspension, even for large volumes. Moreover, the presence of salts in the medium does not disrupt the rheological state of the gel. The result is that such a carboxyvinyl/galactomannan polymer combination makes it possible to widen the field of application of the polymers of the abovementioned type.

The subject of the present invention is therefore firstly a cosmetic or pharmaceutical composition which comprises at least one gelled (or rigidified) phase, at least one of the said phases containing at least one carboxyvinyl polymer as gelling agent, characterized by the fact that the said carboxyvinyl polymer is combined with at least one polygalactomannan.

The polygalactomannan is chosen especially from the group consisting of carob gum, guar gum and tara gum. It is preferably carob gum.

The carboxyvinyl monomer-based polymer is preferably a cross-linked polyacrylic acid with a molecular mass of between 800,000 and 5,000,000.

In conformity with the present invention, the carboxyvinyl polymer(s) is (or are) present especially in an amount of 0.01 to 2% by weight, preferably 0.1 to 1.0% by weight, of the gelled phase containing it(them). As regards the polygalactomannan(s), it(they) represents(represent) especially 0.01 to 3% by weight, preferably 0.01 to 1.5% by weight of the gelled phase containing it(them).

A quantity of polygalactomannan is added more particularly such that the consistency value of the carboxyvinyl polymer is increased by at least 10% relative to the value obtained with the carboxyvinyl polymer alone.

The composition according to the invention may contain salts which are normally incompatible with the carboxyvinyl polymers. Among these salts, there may be mentioned organic salts such as triethanolamine salicylate, sodium benzoate and sodium salicylate.

In conformity with an embodiment, the composition according to the invention contains a phase gelled by means of the carboxyvinyl polymer(s) and the polygalactomannan (s) in which at least one cosmetically or pharmaceutically active ingredient and/or at least one cosmetically or pharmaceutically acceptable additive is present.

In conformity with another embodiment, the composition according to the invention consists in at least two phases, one being a continuous so-called "external" phase gelled by means of the carboxyvinyl polymer(s), any other phase being a so-called "internal" phase in the form of a more or less viscous liquid which is in the form of at least one inclusion inside the said external phase; an internal phase may consist of a thickened or gelled liquid aqueous formulation, an oil-in-water or water-in-oil emulsion, an aqueous dispersion of vesicles consisting of ionic or non-ionic lipid layers encapsulating an aqueous phase, or liquid crystals; the said internal phase(s) may contain at least one cosmetically or pharmaceutically active ingredient and/or at least one cosmetically or pharmaceutically acceptable additive.

In this case, the internal phase(s) advantageously represents(represent) 0.1 to 25% by weight of the said composition.

The abovementioned vesicles are well known and are prepared from a lipid phase comprising at least one ionic and/or nonionic amphiphilic lipid optionally combined with at least one stabilizing additive, and they contain an encapsulated phase which may contain cosmetically or pharmaceutically active products such as moisturizing agents or soothing agents.

Among the nonionic lipids which may be used, there may be mentioned:

(1) linear or branched polyglycerol ethers of formula:

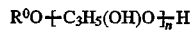

in which:
—$C_3H_5(OH)O$ is represented by the following structures taken together or separately:

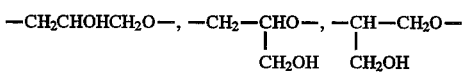

$\bar{n}$ is a mean statistical value between 2 and 6;
$R^0$ represents:
(a) a linear or branched, saturated or unsaturated aliphatic chain containing 12 to 18 carbon atoms;
(b) a residue $R^1CO$, where $R^1$ is a linear or branched $C_{11}$–$C_{17}$ aliphatic radical;
(c) a residue

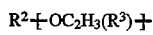

where:
$R^2$ may have the meaning (a) or (b) given for $R^0$;
$OC_2H_3(R^3)$— is represented by the following structures taken together or separately:

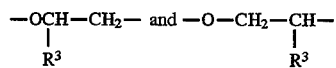

where $R^3$ has the meaning (a) given for $R^0$;
(2) polyoxyethylenated fatty alcohols;
(3) esters of optionally polyoxyethylenated polyols;
(4) cerebrosides; and
(5) oxyethylenated polyglycerol stearate;
(6) polyoxyethylenated sterols.

Among the ionic amphiphilic lipids which may be used, there may be mentioned:
phosphoaminolipids;
glycolipids;
natural phospholipids such as egg or soybean lecithin, sphingomyelin, phosphatidylserine, dipalmitoylphosphatidylcholine and hydrogenated lecithins.

The stabilizing additive is intended, in the known manner, to modify the permeability and/or the surface charge of the vesicles. It is preferably chosen from the group consisting of sterols and anionic stabilizers. The sterol is advantageously cholesterol. The anionic stabilizer is advantageously chosen, on the one hand, from the monosodium or disodium salts (of $C_{14}$–$C_{22}$ acyl) glutamates such as the monosodium salt of N-stearoyl-glutamic acid, the disodium salts with acyl radicals of copra and tallow or alternatively the cocoyl and stearoyl radicals, and, on the other hand, from the phosphoric esters of $C_{12}$–$C_{22}$ fatty alcohols. In a known manner, both a sterol and an anionic stabilizer may be added to the amphiphilic lipid(s).

In the case where one of the internal phases is thickened, the thickening agent(s) used for this purpose is (or are) chosen from the group consisting of cross-linked polyacrylic acids, for example those marketed under the name of "CARBOPOL", cellulose derivatives, for example hydroxypropyl cellulose, carboxymethylcellulose, hydroxyethyl cellulose or hydroxypropyl methylcellulose, mixtures of cetylstearyl alcohol and oxyethylenated cetylstearyl alcohol (for example containing 33 moles of ethylene oxide), acrylamide/sodium acrylate copolymers and vinylpyrrolidone/vinyl acetate copolymers. This (or these) thickening agent(s) is (or are) generally present in an amount of 1 to 10% by weight relative to the total weight of the phase which is thickened.

The active ingredients which are referred to above are chosen especially from slimming agents, moisturizing agents, fixing agents in the hair domain, agents for protecting against sunlight and any agent for the care of the skin and the hair (vitamins, trace elements, plant extracts and the like).

As regards the additives which are referred to above, they are chosen especially from the group consisting of emollients, perfumes, pH modifiers, preservatives and sequestrants.

A process for manufacturing the composition as defined above is characterized by the fact that a gelled or rigidified phase is prepared by incorporation of an aqueous solution of at least one polygalactomannan into an aqueous gel based on at least one carboxyvinyl polymer, before or after neutralization of the latter, for example with an inorganic or organic base, that at least one cosmetically or pharmaceutically active ingredient and/or at least one cosmetically or pharmaceutically acceptable additive is optionally incorporated before or after the said neutralization, and that, where appropriate, the mixture is diluted with water in order to obtain, after 1 to 5 days, a transparent and rigid gel into which at least one viscous phase is optionally injected in order to form at least one inclusion inside the said gel.

A study of the rheology of various aqueous carob gum-cross-linked polyacrylic acid mixtures was carried out. This study shows the variation of the consistency value and of the initial yield point of these mixtures with increase in the level of carob gum. A significant increase is observed in these two parameters. This results in a behavior close to that of the solid for the gels from 0.1% by weight of carob gum: the latter are more rigid and more fragile.

The procedure and the results are given below: the rheological behavior of the gels prepared as in Example 1, but without incorporation of active ingredient or additive, was studied under continuous shearing by means of the MS DIN 14 system at 25° C. A shear cycle is applied to the sample for 2 minutes from 0 to 5 s$^{-1}$ and back to 0. The measurements are carried out several times, for two successive passes, and are also completed by a shear ramp of 5 to 500 s$^{-1}$. The yield curves obtained are analyzed with the HERSCHEL-BULKLEY model, using the equation below, so as to be compared with each other:

$$\tau = \tau_0 + KD^n$$

where:

K=consistency value;

n=yield value;

$\tau_0$=initial yield point;

The consistency value and the initial yield point are the two parameters which reflect the "solid" character of the mixtures studied.

TABLE I

RHEOLOGICAL STUDY

| Cross-linked polyacrylic acid (*) (% by weight) | Carob gum (% by weight) | Consistency index K | Initial yield point 0 |
| --- | --- | --- | --- |
| 0.3 | — | 18.6 | 12.3 |
| 0.3 | 0.05 | 24.6 | 17.8 |
| 0.3 | 0.1 | 25 | 16.7 |
| 0.3 | 0.2 | 33.3 | 23 |
| 0.6 | — | 39.7 | 23.5 |
| 0.6 | 0.05 | 51.3 | 33.7 |
| 0.6 | 0.1 | 51 | 32.3 |
| 0.6 | 0.2 | 63.2 | 35.5 |

(*): Product marketed under the name "CARBOPOL 940" by the company "GOODRICH"

Remark: Solutions of carob gum at 0.05, 0.1 and 0.2% by weight are liquid. (At 1% by weight, this liquid is slightly gelatinous).

The invention therefore relates to combinations (carboxyvinyl-galactomannan polymer(s)) which make it possible to obtain an increase in the consistency value of the polymer gel of at least 10% of its initial value.

Also studied was the behavior of various gels in the presence of salts incompatible with the polymers based on carboxyvinyl monomers. For that, triethanolamine salicylate was added, to 2.35% by weight, to these different gels prepared as above. This salt may be used as bacteriostatic or solubilizer of certain cosmetic active ingredients. Its incompatibility with the polymers of the abovementioned type causes an irreversible fluidification of the gels which become instantly turbid. Table II below presents the results of various trials carried out:

TABLE II

STUDY OF THE BEHAVIOR OF THE GELS IN THE PRESENCE OF SALTS

| Cross-linked polyacrylic acid (*) (% by weight) | Carob gum (% by weight) | Appearance of the gel in the presence of salt |
| --- | --- | --- |
| 0.3 | — | Incompatibility Turbid product - without viscosity |
| — | 0.013 | No viscosity = Liquid product |
| 0.6 | — | Incompatibility Turbid product - free-flowing (After 2 months viscosity unchanged) |

TABLE II-continued

STUDY OF THE BEHAVIOR OF THE GELS IN THE PRESENCE OF SALTS

| Cross-linked polyacrylic acid (*) (% by weight) | Carob gum (% by weight) | Appearance of the gel in the presence of salt |
| --- | --- | --- |
| 0.6 | 0.013 | Rigid and transparent product Viscosity: 12 poises (After 2 months, viscosity unchanged) |
| 0.9 | — | Slightly turbid product Flowability - Viscosity: 22 poises |
| 0.9 | 0.013 | Rigid and fragile gel - Viscosity: 29 poises (After 2 months, greatly increased viscosity) |

(*): Product marketed under the name "CARBOPOL 940" by the company "GOODRICH"

It should be noted that with a very small amount of carob gum (0.013% by weight), the effects of this incompatibility are eliminated for a mean polymer level of 0.6% by weight. A greater resistance of the polymer can be concluded when it is combined with carob gum.

Figure 2:
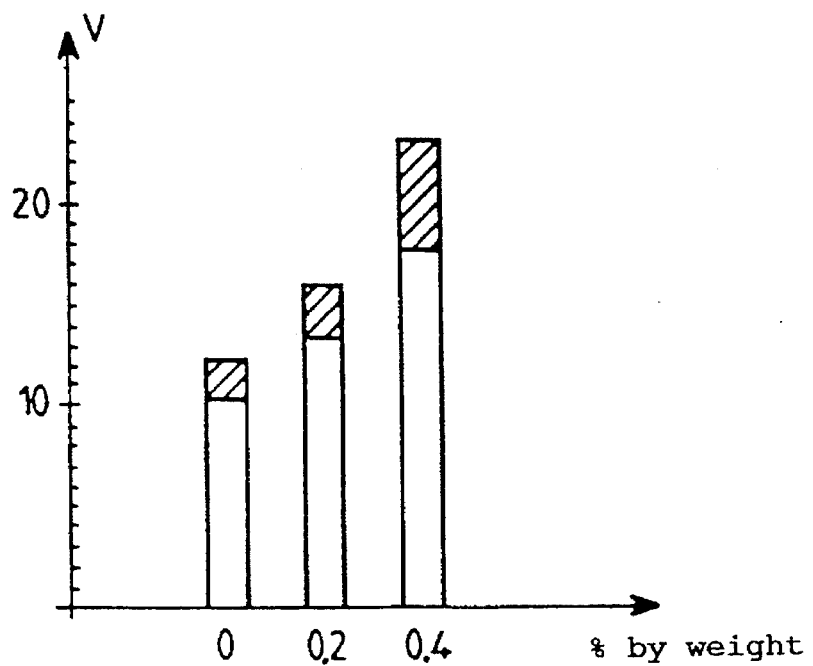

FIG. 1 of the accompanying drawing shows the influence of the addition of 0.15% by weight of carob gum to a cross-linked polyacrylic acid-based gel (CARBOPOL 940) containing 2.35% by weight of triethanolamine salicylate. The percentage by weight of polyacrylic acid is plotted on the x-axis and the consistency value I according to Herschel-Bukley on the y-axis. The curves in a broken and solid line correspond to a gel without addition and with addition of carob gum, respectively. FIG. 2 shows the viscosity V (in poises) measured with a Brookfield-Mobile 3 viscometer at 1 min (shaded zone) and at 10 min (unshaded zone), as a function of the percentage by weight of carob gum, of an emulsion containing 2.35% by weight of triethanolamine salicylate as well as 0.8% cross-linked polyacrylic acid (CARBOPOL 940).

These two figures therefore show that the addition of carob gum makes it possible to compensate the incompatibility of the salt used with cross-linked polyacrylic acid, resulting in a fluidification of the gel based on the said polyacrylic acid. The combination of carob gum with the latter makes it possible to reinforce greatly the apparent viscosity of the gel.

In order to allow the subject of the invention to be understood more clearly, several embodiments will now be described by way of purely illustrative examples with no limitation being implied.

EXAMPLE 1

Slimming Gel

The following formulation is prepared:

| | |
| --- | --- |
| Cross-linked polyacrylic acid (MW 4,000,000), marketed under the name of "CARBOPOL 940" by the company "GOODRICH | 0.6 g |
| Carob gum, marketed under the name of "GENU GUM RL 200" by the company "HERCULES" | 0.02 g |
| Methyl para-hydroxybenzoate | 0.02 g |
| Alga extract | 10 g |
| Ivy extract | 10 g |
| Imidazolidinyl urea, marketed under the name of "GERMALL 115" by the company "SUTTON LABS" | 0.2 g |
| Triethanolamine | 0.6 g |
| Demineralized water q.s. | 100 g |

The cross-linked polyacrylic acid is swollen in 20 g of water, with heating, in order to obtain a thick liquid to which are added methyl para-hydroxybenzoate, alga and ivy extracts and preservative, and then triethanolamine. A transparent gel is obtained.

In parallel, the carob gum powder is swollen in 10 g of water, with heating, in order to obtain a whitish liquid.

The transparent gel and the whitish liquid are mixed, it is diluted with the remaining quantity of water and, after a few days, a transparent and rigid gel is obtained.

EXAMPLE 2

Eye Contour Gel

The following formulation is prepared:

| | |
| --- | --- |
| Cross-linked polyacrylic acid (MW 1,250,000), marketed under the name of "CARBOPOL 941" by the company "GOODRICH" | 0.7 g |
| Carob gum, marketed under the name of "GELLOID LB 100" by the company "MARINE COLLOIDS" | 0.015 g |
| Caffeine | 0.5 g |
| Sodium benzoate | 0.5 g |
| Imidazolidinyl urea, marketed under the name of "GERMALL 115" by the company "SUTTON LABS" | 0.2 g |
| Hamamelis oil | 0.015 g |
| Triethanolamine | 0.7 g |
| Demineralized water q.s. | 100 g |

The procedure is carried out as in Example 1 except that the triethanolamine is incorporated after mixing the cross-linked polyacrylic acid-based transparent gel and the whitish liquid consisting of the carob gum powder swollen in water with heating.

A transparent and rigid gel is also obtained.

Examples 3 to 14 below relate to slimming compositions containing two immiscible viscous phases (A) and (B). The so-called internal phase (A) contains the active ingredient(s) and is dispersed, in the form of inclusions, inside the so-called external phase (B) which consists of a gel conforming to the present invention. The phase (A) should have a viscosity which is greater than 10 poises.

In order to manufacture these compositions, the machine as described in French Patent No. 2,634,688 is used which comprises a rotating tray intended to receive a jar for containing a gel and an inclusion product, and means for injecting the inclusion product into the jar, with a possibility of a relative movement between the tray and the said means for injecting the product following a direction substantially orthogonal to the tray. Initially, the jars are sealed with gel (phase (B)) so that no air bubble is trapped in the gel mass or at the gel/jar wall interface.

EXAMPLE 3

Slimming Product of the Inclusion-Containing Gel Type

A slimming composition containing, as phase (A), an oil-in-water emulsion is prepared. The weight ratio of the phase (A) to the phase (B) is 10/90. Each of the phases is formulated as follows:

Internal phase (A):

| | | |
|---|---|---|
| Cyclomethicone, commercialized under the name of "VOLATIL SILICONE 7158" by the company "UNION CARBIDE" | 10 | g |
| Perhydrosqualene | 18 | g |
| Vaseline oil | 5 | g |
| Liquid lanolin | 4 | g |
| Glyceryl stearate + polyethylene-glycol (100 units) stearate, marketed under the name "ARLACEL 165" by the company "ATLAS" | 6 | g |
| Product marketed under the name "TWEEN 60" by the company "ICI" | 2 | g |
| Cetyl alcohol | 1.2 | g |
| Stearic acid | 2.5 | g |
| Triethanolamine | 0.01 | g |
| Preservative | 0.3 | g |
| Antioxidants | 0.3 | g |
| Demineralized water q.s. | 100 | g |
| Caffeine | 1 | g |
| Gingko biloba extract, marketed by the compnay "INVERNI" | 0.5 | g |
| Propylene glycol | 5 | g |

An oil-in-water emulsion is prepared from the above formulation, the procedure being carried out in a standard manner.

Phase (B)

| | | |
|---|---|---|
| Cross-linked polyacrylic acid (MW 4,000,000) marketed under the name of "CARBOPOL 940" by the company "GOODRICH" | 0.3 | g |
| Carob gum, marketed under the name of "GENU GUM RL 200-COPENHAGEN PECTIN" by the company "HERCULES" | 0.05 | g |
| Triethanolamine | 0.3 | g |
| Sterile demineralized water q.s. | 100 | g |
| Preservatives | 0.3 | g |

The polyacrylic acid is swollen in 15 g of water, with heating, then the preservatives and then the triethanolamine are added into the thick liquid obtained in order to obtain a transparent gel.

In parallel, the carob gum powder is swollen in 10 g of water, with heating, in order to obtain a whitish liquid.

The two compositions obtained are mixed, they are diluted with the remaining quantity of water and, after a few days, a transparent and rigid gel is obtained.

The phase (A) is then injected into a 150 ml jar with a wide opening, containing the gel phase (B) thus obtained.

An attractive visual appearance is obtained. The jar is allowed to stand for 48 hours to allow stabilization of the transparent gel of phase (B).

No movement of the phase (A) is observed inside the phase (B) after transportation and when the jar is subjected to slight impact.

EXAMPLE 4

Slimming Product of the Inclusion-Containing Gel Type

A slimming composition containing, as phase (A), an oil-in-water emulsion is prepared. The phase (B) is formulated as in Example 3. The phase (A) is formulated as follows, the weight ratio of the phase (A) to the phase (B) being 15/85:

Phase (A):

| | | |
|---|---|---|
| Demineralized water q.s. | 100 | g |
| Propylene glycol | 2 | g |
| Polyethylene glycol with a molecular mass of 400 | 3 | g |
| Gingko biloba extract, marketed by the company "INVERNI" | 0.3 | g |
| Caffeine | 3 | g |
| Sodium benzoate | 3 | g |
| Preservative | 0.3 | g |
| Perfume | 0.5 | g |
| Cross-linked polyacrylic acid (MW 1,250,000), marketed under the name of "CARBOPOL 941" by the company "GOODRICH" | 0.2 | g |
| Isopropyl myristate | 1 | g |
| Cetyl alcohol | 3 | g |
| Stearic acid | 3 | g |
| Glycerol monostearate | 3 | g |
| Maize germ oil | 2 | g |

The oil-in-water emulsion of the phase (A) is prepared in the standard manner. A jar of phase (B) gel is then prepared containing inclusions of phase (A), in the same manner as in Example 3, and the same observations are made with regard to the stability of the inclusions of phase (A) inside phase (B).

EXAMPLE 5

Slimming Product of the Inclusion-Containing Gel Type

A slimming composition containing, as phase (A), a water-in-oil emulsion is prepared. The phase (B) is identical to that of Example 3. The weight ratio of the phase (A) to the phase (B) is 1/99. The phase (A) is formulated as follows:

Phase (A):

| | | |
|---|---|---|
| Product marketed under the name "PROTEGIN X" by the company "GOLDSCHMIDT" | 20 | g |
| Vaseline oil | 10 | g |
| Aromatic composition | 1 | g |
| Sunflower oil | 15 | g |
| Preservative | 0.3 | g |
| Demineralized water q.s. | 100 | g |
| Glycerol | 5 | g |
| Magnesium sulfate | 0.5 | g |
| Extract of the ivy Saponnes totales, marketed by the company "INVERNI" | 0.5 | g |
| Product marketed under the name "CETIOL HE" by the company "HENKEL" | 4 | g |

The water-in-oil emulsion of the phase (A) is prepared in a standard manner. A jar of phase (B) gel is then prepared containing inclusions of phase (A), in the same manner as in Example 3, and the same observations are made with regard to the stability of the inclusions of phase (A) inside the phase (B).

EXAMPLE 6

Slimming Product of the Inclusion-Containing Gel Type

A slimming composition containing, as phase (A), a water-in-oil emulsion is prepared. The phase (B) is identical to that of Example 3. The weight ratio of the phase (A) to the phase (B) is 5/95. The phase (A) is formulated as follows:

Phase (A):

| | | |
|---|---|---|
| Product marketed under the name "ABIL WE 09" by the company "GOLDSCHMIDT" | 5 | g |
| Isopropyl myristate | 5 | g |
| Cyclomethicone, marketed under the name "VOLATIF SILICONE 7188" by the company "UNION CARBIDE" | 8 | g |
| Vaseline oil | 5 | g |
| Colloidal silica, marketed under the name "AEROSIL R 812" by the company "DEGUSSA AG" | 0.4 | g |
| Purcellin oil, marketed by the company "DRAGOCOCO" | 14 | g |
| Demineralized water q.s. | 100 | g |
| Sodium chloride | 0.5 | g |
| Diethylene glycol monomethyl ether, marketed under the name "TRANSCUTOL" by the company "GATTEFOSSE" | 3 | g |
| Gingko biloba extract, marketed by the company "INVERNI" | 0.5 | g |
| Caffeine | 1 | g |
| Sodium hydroxide | 0.008 | g |
| Preservative | 0.3 | g |

The oil-in-water emulsion of the phase (A) is prepared in a standard manner. A jar of phase (B) gel is then prepared containing inclusions of phase (A), in the same manner as in Example 4, and the same observations are made with regard to the stability of the inclusions of phase (A) inside the phase (B).

EXAMPLE 7

Slimming Product of the Inclusion-Containing Gel Type

A slimming composition containing, as phase (A), an emulsified oil-in-water gel is prepared. The phase (B) is identical to that of Example 3. The weight ratio of the phase (A) to the phase (B) is 10/90. The phase (A) is formulated as follows:

Phase (A):

| | |
|---|---|
| Cross-linked polyacrylic acid (MW 4,000,000), marketed under the name of "CARBOPOL 940" by the company "GOODRICH" | 0.6 g |
| Cyclomethicone, marketed under the name "VOLATIL SILICONE 7158" by the company "UNION CARBIDE" | 3 g |
| Purcellin oil, marketed by the company "DRAGOCOCO" | 7 g |
| Product marketed under the name "TEFOSE 63" by the company "GATTEFOSSE" | 3 g |
| Preservative | 0.3 g |
| Perfume | 0.4 g |
| Ethyl alcohol | 10 g |
| Triethanolamine | 0.2 g |
| Demineralized water q.s. | 100 g |
| Caffeine | 1 g |
| Product marketed under the name "CETIOL HE" by the company "HENKEL" | 2 g |
| Standard Gingko biloba extract, marketed by the company "INVERNI" | 0.8 g |

The emulsified oil-in-water gel of the phase (A) is prepared in the standard manner. A jar of phase (B) gel is then prepared containing inclusions of phase (A), in the same manner as in Example 4, and the same observations are made with regard to the stability of the inclusions of phase (A) inside the phase (B).

EXAMPLE 8

Slimming Product of the Inclusion-Containing Gel Type

A slimming composition containing, as phase (A), an aqueous dispersion of vesicles containing nonionic lipid layers encapsulating an aqueous phase with an active agent content is prepared. The phase (B) is the same as that of Example 3. The weight ratio of the phase (A) to the phase (B) is 25/75. The cream forming the phase (A) is prepared in two stages:

First stage: Preparation of an aqueous dispersion of vesicles

A lipid phase formulated as follows is used:

| | |
|---|---|
| Polyglycerol-3 cetyl ether | 3.8 g |
| β-Sitosterol | 3.8 g |
| Dicetyl phosphate | 0.4 g |

The mixture with the above formulation is melted while stirring gently at a temperature of 95°–100° C. and 16 g of water, heated to 90° C. are introduced into the molten mixture, with slow stirring, after which the mixture is vigorously stirred in a turbine equipped with blades until a whitish gelled mass is obtained.

1.5 g of caffeine and 16 g of water are then added at 20° C. The temperature and the stirring are maintained for 60 minutes.

The mixture is allowed to mature.

10 g of water containing 0.3 g of a preservative are introduced at 40° C. and the mixture is again allowed to mature.

Second stage: The following formulation is prepared:

| | | |
|---|---|---|
| Aqueous dispersion of vesicles obtained at the first stage | 50 | g |
| Sodium benzoate | 1.5 | g |
| Diethylene glycol monomethyl ether, marketed under the name "TRANSCUTOL" by the company "GATTEFOSSE" | 3 | g |
| Acidic escin, marketed by the company "INVERNI" | 0.5 | g |
| Sodium hydroxide | 0.007 | g |
| Water-soluble plant extract of ivy, marketed by the company "GATTEFOSSE" | 3 | g |
| Sunflower oil | 35 | g |
| Perfume | 0.6 | g |
| Cross-linked polyacrylic acid (MW 4,000,000) marketed under the name of "CARBOPOL 940" by the company "GOODRICH" (thickening agent) | 0.02 | g |
| Triethanolamine | 0.2 | g |
| Water q.s. | 100 | g |

The sunflower oil and the perfume are introduced into the aqueous dispersion of vesicles obtained in the first stage, at 30° C. and the mixture is stirred in the turbine and allowed to mature.

Finally, the mixture is thickened by adding a gel consisting of a thickening agent dissolved in water.

This phase (A) is then injected into the phase (B). A jar of inclusion-containing slimming product is obtained on which the same observations are made as in the preceding examples, with regard to the stability of the inclusions.

EXAMPLES 9 TO 14

The following formulation is prepared for a phase (B):

| | | |
|---|---|---|
| Cross-linked polyacrylic acid (MW 1,250,000), marketed under the name of "CARBOPOL 941" by the company "GOODRICH" | 0.6 | g |
| Guar gum | 0.2 | g |
| Triethanolamine | 0.6 | g |
| Sterile demineralized water q.s. | 100 | g |
| Preservatives | 0.2 | g |
| Triethanolamine salicylate | 2.35 | g |

A phase (B) gel is prepared as indicated in Example 3.

A procedure is carried out as in Examples 3 to 8, respectively, by replacing the phase (B) of these examples with the phase (B) above. The same observations are made with regard to the rigidity of the gel and the stability of the inclusions.

EXAMPLE 15

The yield point of the gels prepared as in Example 1 but without incorporation of active ingredients as explained for Table I, was measured according to the Herschel-Bulkley model for the following compositions:

1—a gel prepared with 0.3% by weight of carboxyvinyl polymer sold under the name "CARBOPOL 940" by the company "GOODRICH", 2—a gel prepared from 0.3% by weight of "CARBOPOL 940" and 0.1% carob gum, 3—a gel prepared from 0.3% by weight of "CARBOPOL 940" and 0.1% xanthan gum.

Figure 3:
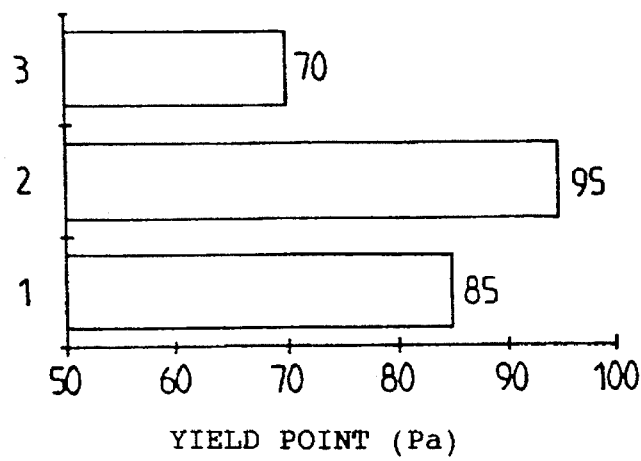

The results are given in the graph of FIG. 3. It can be seen that the addition of xanthan gum does not modify the yield point of carbopol, there is in fact, on the contrary, fluidification whereas the addition of carob gum clearly modifies this yield point.

EXAMPLE 16

Figure 4:
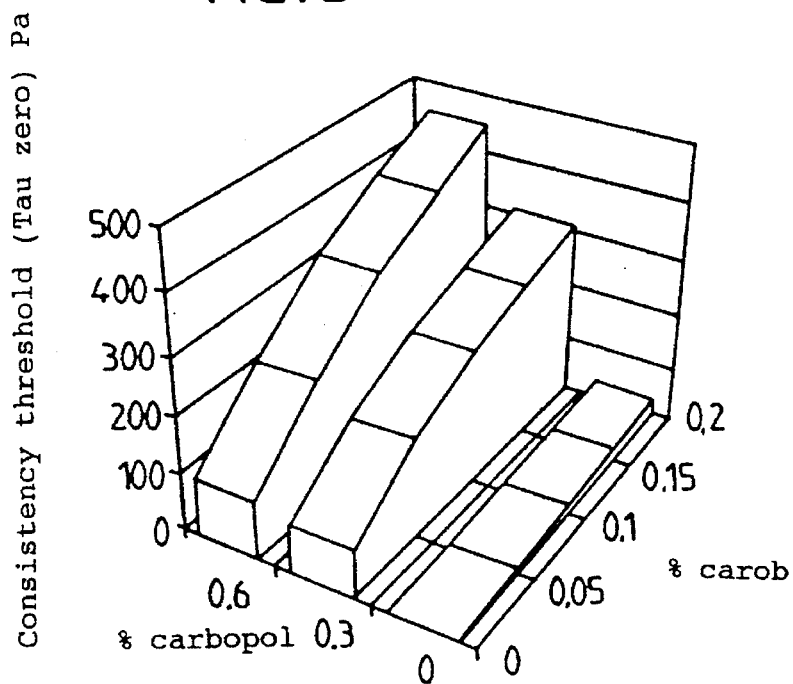

The initial yield point, in pascals, of compositions containing increasing quantities of "CARBOPOL 940" and carob gum, was measured as in Example 15. The results obtained are represented in FIG. 4. It can be seen that the addition of carob makes it possible to increase very clearly the yield point.

EXAMPLE 17

Figure 5:
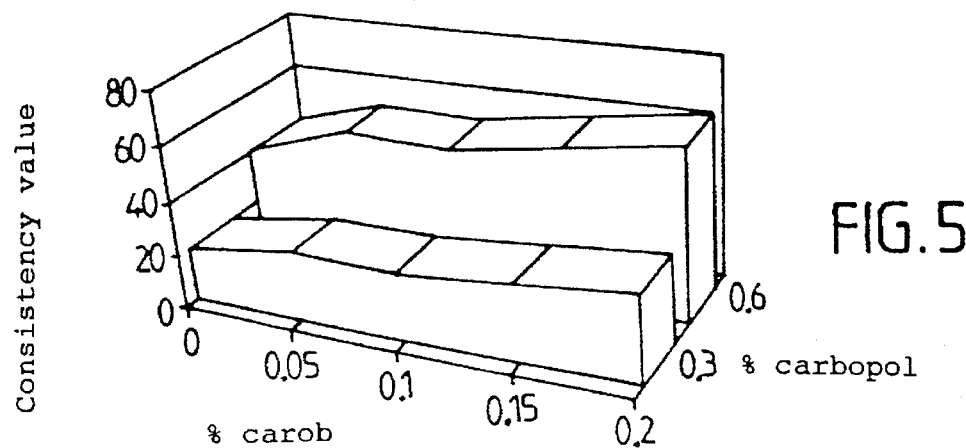

The consistency value was also measured according to the Herschel-Bulkey model. The results obtained are represented in FIG. 5. It can be seen that the consistency value of a carob gel increases significantly by addition of a small amount of carob gum.

I claim:

1. A cosmetic or pharmaceutical composition comprising at least one rigid gelled phase which, when subjected to shear, yields a mild and non-sticky product, said gelled phase comprising at least one carboxyvinyl polymer present in an amount ranging from 0.3 to 0.9 percent by weight based on the weight of said gelled phase, and, said gelled phase further comprising carob gum in an amount of from 0.05 to 0.4 percent by weight based on the weight of said gelled phase, wherein said carboxyvinyl polymer is a cross-linked polyacrylic acid having a molecular mass ranging from 800,000 to 5,000,000.

2. The composition according to claim 1, wherein said rigid gelled phase further comprises an organic salt selected from the group consisting of triethanolamine salicylate, sodium benzoate and sodium salicylate.

3. The composition according to claim 1 wherein said carboxyvinyl polymer and carob gum are present in an amount to produce an increase of consistency of at least 10% relative to the consistency of said composition in the absence of said carob gum.

4. The composition according to claim 1 further comprising at least one of a cosmetically or pharmaceutically active ingredient and a cosmetically or pharmaceutically acceptable additive.

5. The composition according to claim 1 further comprising at least one other phase such that said gelled phase is a continuous external phase and said at least one other phase is an internal liquid or viscous phase.

6. The composition according to claim 5 wherein said internal phase comprises a thickened or gelled or liquid aqueous water-in-oil or oil-in-water emulsion, an aqueous dispersion of vesicles comprising ionic or nonionic liquid layers encapsulating an aqueous phase, or liquid crystals.

7. The composition according to claim 6 wherein said internal phase further contains at least one of a cosmetically or pharmaceutically active ingredient and a cosmetically or pharmaceutically acceptable additive.

8. The composition according to claim 5 wherein said internal phase is present in an amount of 0.1 to 25% by weight of said composition.

9. The composition according to claim 4 wherein said active ingredient is selected from the group consisting of slimming agents, moisturizing agents, fixing agents, sunlight protecting agents, skin care agents and hair care agents.

10. The composition according to claim 7 wherein said active ingredient is selected from the group consisting of slimming agents, moisturizing agents, fixing agents, sunlight protecting agents, skin care agents and hair care agents.

11. The composition according to claim 4 wherein said additive is selected from the group consisting of emollients, perfumes, pH modifiers, preservatives and sequestrants.

12. The composition according to claim 7 wherein said additive is selected from the group consisting of emollients, perfumes, pH modifiers, preservatives and sequestrants.

13. A process for making a cosmetic or pharmaceutical composition comprising at least one rigid gelled phase which, when subjected to shear, yields a mild and non-sticky product, said process comprising mixing at least one carboxyvinyl polymer and carob gum in sufficient quantities to produce said gelled phase containing 0.3 to 0.9 percent by weight of said gelled phase of said carboxyvinyl polymer and 0.05 to 4% by weight based on the weight of said gelled phase of said carob gum, where said carboxyvinyl polymer is a cross-linked polyacrylic acid having a molecular mass ranging from 800,000 to 5,000,00.

* * * * *